(12) United States Patent
Laser et al.

(10) Patent No.: US 9,962,064 B2
(45) Date of Patent: May 8, 2018

(54) ADAPTER FOR ENDOSCOPY

(71) Applicant: Xion GmbH, Berlin (DE)

(72) Inventors: Helmut Laser, Berlin (DE); Holger Muller, Glienicke-Nordbahn (DE)

(73) Assignee: XION GMBH, Berlin (DE)

( * ) Notice: Subject to any disclaimer, the term of this patent is extended or adjusted under 35 U.S.C. 154(b) by 202 days.

(21) Appl. No.: 14/930,989

(22) Filed: Nov. 3, 2015

(65) Prior Publication Data

US 2016/0128550 A1 May 12, 2016

(30) Foreign Application Priority Data

Nov. 10, 2014 (DE) .......................... 10 2014 222 880

(51) Int. Cl.
*A61B 1/00* (2006.01)
*A61B 1/04* (2006.01)

(52) U.S. Cl.
CPC ...... *A61B 1/00128* (2013.01); *A61B 1/00126* (2013.01); *A61B 1/00142* (2013.01); *A61B 1/00193* (2013.01); *A61B 1/042* (2013.01); *A61B 1/00105* (2013.01)

(58) Field of Classification Search
CPC .. A61B 1/001; A61B 1/00126; A61B 1/00128
USPC ........................................ 600/109, 111–112
See application file for complete search history.

(56) References Cited

U.S. PATENT DOCUMENTS

| 4,323,304 A | * | 4/1982 | Ishii | .................... | A61B 1/00128 |
| | | | | | 396/17 |
| 4,574,783 A | * | 3/1986 | Kazuhiro | ............... | A61B 1/121 |
| | | | | | 600/112 |
| 4,611,888 A | * | 9/1986 | Prenovitz | ............... | A61B 1/042 |
| | | | | | 348/75 |
| 4,756,304 A | | 7/1988 | Watanabe | | |
| 4,807,594 A | * | 2/1989 | Chatenever | ........ | A61B 1/00195 |
| | | | | | 359/513 |
| 4,844,071 A | * | 7/1989 | Chen | ...................... | A61B 1/042 |
| | | | | | 600/112 |
| 5,101,807 A | * | 4/1992 | Kawashima | ....... | A61B 1/00195 |
| | | | | | 385/43 |

(Continued)

FOREIGN PATENT DOCUMENTS

| DE | 9300529 U1 | 3/1993 |
| DE | 10 2006 045 032 B3 | 5/2008 |
| EP | 2563203 A1 | 3/2013 |

*Primary Examiner* — Matthew J Kasztejna
(74) *Attorney, Agent, or Firm* — Ware, Fressola, Maguire & Barber LLP

(57) ABSTRACT

An adapter for the releasable and relockable coupling of an endoscope with a camera head has an inner wall and an outer wall that are connected with one another via a connecting wall extending between the inner wall and outer wall at or near their first axial ends, and which inner wall and outer wall are arranged with at least a lateral separation from one another, so that an open clearance results between the inner wall and outer wall on a second axial side that is situated opposite the first axial ends. Furthermore, the adapter comprises a coupling wall that seals a clearance enclosed by the inner wall at or near a second axial end of the inner wall, such that the clearance that is enclosed by the inner wall is open at a first axial side that is situated opposite the second axial end of the inner wall.

15 Claims, 12 Drawing Sheets

(56) References Cited

U.S. PATENT DOCUMENTS

| | | | | |
|---|---|---|---|---|
| 5,156,141 A | * | 10/1992 | Krebs | G02B 23/2476 600/112 |
| 5,433,221 A | | 7/1995 | Adair | |
| 5,498,230 A | | 3/1996 | Adair | |
| 5,682,199 A | * | 10/1997 | Lankford | A61B 1/00105 348/65 |
| 5,702,350 A | | 12/1997 | Vry et al. | |
| 5,743,847 A | * | 4/1998 | Nakamura | A61B 1/00193 600/111 |
| 5,792,045 A | | 8/1998 | Adair | |
| 5,846,186 A | * | 12/1998 | Upsher | A61B 1/267 600/112 |
| 6,030,339 A | | 2/2000 | Tatsuno et al. | |
| 6,080,101 A | | 6/2000 | Tatsuno et al. | |
| 6,179,479 B1 | | 1/2001 | Crivelli | |
| 6,676,598 B2 | * | 1/2004 | Rudischhauser | A61B 1/267 600/188 |
| 9,468,367 B2 | * | 10/2016 | Ouyang | A61B 1/00103 |
| 9,622,646 B2 | * | 4/2017 | Ouyang | A61B 1/00103 |

* cited by examiner

ADAPTER FOR ENDOSCOPY

CROSS REFERENCE TO RELATED APPLICATION

This application claims priority under 35 USC § 119 to German Patent Application No. 102014222880.8 filed on Nov. 10, 2014, which application is hereby incorporated by reference in its entirety.

SUBJECT MATTER OF THE INVENTION

The invention relates to an adapter for coupling between exchangeable endoscopes and camera heads. Due to this function, such adapters are also called intermediate adapters, couplers, endoscope couplers or camera couplers.

BACKGROUND OF THE INVENTION

In endoscopy, apparatuses which come into contact with the patient or the sterile medical personnel must be kept sterile to avoid infections. Therefore, endoscopes are sterilized before use and camera heads and camera cables are provided with a non-reusable sterile covering made of plastic. Sterile adapter systems may be used for a secure separation between the sterile outside of such coverings and the non-sterile inside of such coverings. Sterile endoscopes connected to the camera head may thereby be exchanged quickly and comfortably without needing to interrupt the sterile barriers to the non-sterile camera head.

A sterile covering with optical window is known from U.S. Pat. No. 5,433,221 A.

The connection of a camera head with a sterile endoscope via a special sterile intermediate adapter and a sterile covering of the camera head is known from U.S. Pat. No. 5,498,230 and U.S. Pat. No. 5,792,045. A special sterile intermediate adapter with lead-throughs for exposure light is known from U.S. Pat. No. 4,756,304A.

A camera adapter for stereo endoscopes is known from U.S. Pat. No. 5,702,350.

An adapter for two-channel stereo endoscopes is known from EP 2563203 A4.

A special sterile intermediate adapter for stereo endoscopes is known from DE 9300529 U1.

SUMMARY OF THE INVENTION

The object of the invention is to provide an improved adapter and an improved adapter system, comprising an endoscope, an adapter and a camera head.

According to the invention, this object is achieved by an adapter for releasable and relockable coupling of an endoscope with a camera head. The adapter comprises an inner wall and an outer wall that are connected with one another via a connecting wall extending between said inner wall and outer wall at or near their first axial ends, and which inner wall and outer wall are arranged with at least a lateral separation from one another so that an open clearance results between said inner wall and outer wall, on a second axial side that is situated opposite the first axial ends. Furthermore, the adapter comprises a coupling wall that seals a clearance enclosed by the inner wall at or near a second axial end of said inner wall, such that the clearance that is enclosed by the inner wall is open at a first axial side that is situated opposite the second axial end of the inner wall. One of the clearances is designed for coupling with at least a portion of a distal camera head end. The other of the clearances is designed for coupling with at least a part of a proximal endoscope end.

Numerous improvements may be achieved via the design of the adapter. One aspect of the invention is that the optical and mechanical design may be shortened. The optical quality of the imaging and the practical handling of the endoscope are thereby improved. An additional aspect is that the durability, rigidity and precision of the coupling between endoscope and camera head can be increased. An additional aspect of the invention is that a smaller structural size may be enabled. The system consisting of endoscope, adapter and camera head is hereby more manageable. Furthermore, the adapter can be better sterilized and is simpler to handle, such that no operating errors of the adapter occur even under time pressure. For example, in one embodiment of the adapter an exchange of a sterile covering may be simplified. The adapter is suitable for both two-dimensional (2D) and three-dimensional (3D) endoscopy. In three-dimensional (3D) endoscopy, particular requirements arise for the coupling between camera and endoscope due to the use of stereo endoscopes. Depending on the design of the stereo endoscope, a high coupling precision and a safeguard against rotation may be required. In one embodiment of the adapter, the adapter is suitable for use in stereo endoscopes and in particular has for this purpose a rotation safeguard that enables it to establish a sterile system containing a stereo endoscope, adapter and camera head, since the rotation safeguard ensures that the optical channels of the stereo endoscope are aligned towards the optical channels of the camera head. An adjustment effort may hereby be reduced. Furthermore, an embodiment of the adapter has only a few mechanical parts, which may reduce costs. Furthermore, a simpler design of the adapter is thus possible, as well as simpler sterilization.

The inner wall and outer wall may be arranged concentrically relative to one another in at least one lateral plane. Here, "concentrically" is to be understood as being arranged symmetrically around a common center. The shape of the inner wall and outer wall is hereby largely open and limited only by the symmetry condition. In one possible alternative embodiment, the arrangement may also be asymmetrical.

In one possible embodiment of the adapter, the adapter between an endoscope (that can be arranged on a distal side of the adapter) and a camera head (that can be arranged on a proximal side of the adapter) is germ-proof in order to separate a sterile side from a non-sterile side and to keep the sterile side sterile in this way. Here, "germ-proof" is to be understood such that with respect to the adapter no germs can penetrate from one side of the adapter to the other side. Therefore, no germs may thus come from one side of the adapter to the other side. For example, for this a covering may be drawn over the camera head. The camera head is typically on the non-sterile side and is covered with a covering that is non-sterile on an inside of said covering and sterile on the outside of said covering. For example, an endoscope may be arranged on the sterile, distal side of the adapter and a camera head may be arranged on the non-sterile, proximal side of the adapter. In this case, the non-sterile camera head is surrounded by the covering, which is non-sterile on its inside and sterile on its outside, whereby another endoscope can easily be locked to the adapter without negatively affecting the sterility of an adapter system made up of endoscope, adapter and camera head.

In one embodiment of the adapter, at least one of the clearances may have a cross section varying along the axial direction. The variation along the axial direction of the cross section may result in a conical clearance, for example, but alternatively the cross section may also first increase along the axial direction, then reduce in size again and finally enlarge again, such that the tapering of the clearance may be used as an attachment lobe, for example. An embodiment of the clearance with attachment lobe is particularly preferred if at least a portion of the material of the adapter has a reversibly deformable material, for example a plastic material. The adapter may be made of a plastic material that is reversibly deformable, or parts of the adapter may be made from such a material and other parts may be made of non-deformable materials.

For example, the clearance may be cylindrical, in the shape of a hollow cylindrical shell, or have a different geometric shape. What is to be understood here by "cylindrical" are all shapes that have two base surfaces of any shape that have an axial separation from one another and are connected with one another across the axial separation. For example, "cylindrical" includes circular cylindrical, prismatic or other cylindrical shapes.

The adapter has a distal and a proximal end. An endoscope is typically connected to the distal end of the adapter and a camera head is connected to the proximal end of the adapter. In one embodiment of the adapter, at least one distal end of the inner wall and/or outer wall lies in a first plane with a distal end of the adapter. Alternatively or additionally, at least one proximal end of the inner wall and/or outer wall may also lie in a second plane with a proximal end of the adapter. The adapter may also be designed such that the two ends of the inner wall and outer wall lie together in the plane with the ends of the adapter, and thus for the ends of the adapter. Additional modules may also be arranged so that none of the ends of the outer wall and none of the ends of the inner wall forms an end of the adapter. For example, additional modules may be shape elements, attachment elements or coverings. For example, the coverings may be attached to the outer wall of the adapter or be pressed via an attachment element to the outer wall of the adapter so that a hermetically sealed connection is created. Shape elements may serve to continue the shape of the inner wall and/or outer wall.

In one possible embodiment of the adapter, at least one of the clearances has at least one coupling face. The coupling face is designed to couple with another coupling face. For example, one of the clearances may have a surface contour that is matched with a surface contour of a coupling face of an endoscope or camera head to be coupled such that the coupling faces of the clearance of the adapter and of the endoscope or camera head to be coupled couple upon sliding into one another. For example, the coupling may hereby be produced via retention and/or friction forces. Alternatively, the coupling point may be designed as a clearance fit with mechanical coupling slack. Alternatively or additionally, the coupling faces may also be magnetic or have a magnetic material, such that a coupling is possible via magnetic interaction. Each coupling face may have multiple coupling sub-faces. In a coupled state, all coupling sub-faces of the clearance may be engaged with coupling sub-faces of the endoscope or camera head to be coupled. Alternatively, in an only partially coupled state, a portion of the coupling sub-faces of the adapter may also be engaged with corresponding coupling sub-faces of the endoscope or camera head to be coupled. In the partially coupled state, this means that coupling sub-faces may have a separation from the corresponding coupling sub-faces of the coupling partner (meaning of the endoscope or camera head) that is greater than the coupling slack of the adapter. The coupling face may extend axially from a distal end of the clearance up to a proximal end of the clearance. The coupling face may also encompass only a portion of the clearance. The axial extent of the coupling face may thus also include coupling sub-faces that are not engaged.

In a further embodiment, the adapter may be designed to ensure that, in a state in which the adapter is coupled with the endoscope and camera head, the parts of the proximal endoscope end and the parts of the distal camera head end that protrude into one of the respective clearances overlap along the axial direction of the adapter by at least 50% of an axial length of at least one of the clearances. The parts protruding into the respective clearance may couple with the coupling face or with one of the multiple coupling sub-faces of the clearance and form coupled parts.

What are to be understood by coupled parts are all parts of the region of the proximal endoscope end and of the distal camera head end along the axial direction of the adapter that lie between an outermost proximal coupling point and an outermost distal coupling point of the clearance. The coupled part may also comprise sub-faces that are not engaged or, respectively, are uncoupled; for example, part of the surface contour of one of the clearances, said surface contour forming the coupling face, may be executed such that this partial region does not contribute to the coupling.

The inner wall, outer wall, connecting wall and/or coupling wall may have varying wall thicknesses along the axial direction and/or along the polar angle. The cross section of one of the clearances or of both clearances may hereby also vary along the axial direction. For example, in one case the cross section of a clearance may remain constant and that of the other clearance may vary.

The inner wall, outer wall, connecting wall and/or coupling wall may have one or more plane faces. The inner wall, outer wall, connecting wall and/or coupling wall may also have one or more rotation faces, i.e. geometric faces that are generated via rotation around an axis of a curve lying in a plane; said axis being arranged orthogonal to the plane, for example: cylinder faces and/or cylindrical shell faces, cone faces, hyperboloid faces and/or paraboloid faces. The inner wall, outer wall, connecting wall and/or coupling wall may also have one or more faces that may not be generated via rotation of a curve around an axis of a curve lying in a plane, said axis being arranged orthogonal to the plane, for example: prism faces, pyramid faces, polyhedron faces or freeform faces.

In a state in which the adapter is coupled with the endoscope and camera head, the inner wall, outer wall, connecting wall and/or coupling wall may be engaged with parts of the endoscope or camera head, for example in order to form an axial stop. In the state in which the adapter is coupled with the endoscope and camera head, the inner wall, outer wall, connecting wall and/or coupling wall may be distant from parts of the endoscope or camera head, and thus not form an axial stop.

Furthermore, in the state in which the adapter is coupled with the endoscope and camera head, the adapter may be designed such that coupling faces of the endoscope, camera head and adapter overlap in the axial direction by more than 50% of the axial length of the outer wall of the adapter with the outer wall. As a result of the overlap, the adapter is partially double-walled in the radial direction.

A small axial structural length results from the overlap. This pertains not only to the adapter itself but rather to the total system made up of endoscope, adapter and camera head. A very advantageous ratio of guide length and guide diameter to the coupling faces of the endoscope and camera head may thus be realized via the overlap. Seizing and twisting of the coupling may thereby be avoided. In one embodiment, the adapter is designed such that—upon coupling of the adapter—the coupling faces slide easily against one another, which facilitates easy, reliable coupling of the adapter with the endoscope and the camera head.

In one embodiment, the coupling wall may have at least one opening and/or at least one optical window that is designed to transmit radiation in the optical wavelength range. In one possible embodiment of the adapter, the coupling wall has at least one optical window that is designed to transmit radiation in the optical wavelength range. The at least one optical window may be arranged with a window middle point around a coupling wall middle point. Multiple optical windows may be arranged on the coupling wall, for example two optical windows that are matched to the beam paths of a stereo endoscope. Multiple optical windows may also be arranged, or one optical window may have such a large diameter that multiple beam paths (of a stereo endoscope, for example) may be transmitted through the optical window or windows. The proximal side and the distal side of the adapter are separated from one another hermetically (or at least so as to be germ-proof) by the optical window or windows since the optical window or windows only let pass radiation but (for example) no germs, such that the proximal side and the distal side of the adapter may be separated from one another so as to maintain sterility. The coupling wall may also have an opening for light transmission. In this case, germs may penetrate through the opening. The opening may alternatively have an opening window or multiple optical windows that separate the proximal side and the distal side of the adapter hermetically, or at least so as to be germ-proof.

In one possible embodiment of the adapter, the adapter is designed for use of an endoscope without the output of an optical image. In this embodiment, the image transmission may take place as a signal transmission from the camera head or external components via electrical or optical signal lines, or via radio transmission. For signal transmission, the adapter may have openings, plugs, bushings, signal lines, transmission electronics or windows that are transparent to electromagnetic radiation.

In one embodiment of the adapter, the adapter may be designed to be used for power transmission. For power transmission, the adapter may have heat pipes, conduits, glass fibers, Peltier elements, line terminators, ferrite cores, openings, plugs, bushings, electrical conductors, electrical modules, electronic modules, shafts, gears, couplings or windows transparent to electromagnet radiation. A power transmission may take place in any form, in particular thermally, electrically, mechanically, inductively or as radiation. The structural elements for power transmission may be part of the adapter, or may be connected with this so as to be releasable and relockable.

In one possible embodiment, the adapter is designed for transmission of at least one medium, i.e. of a substance in any aggregate state or any appearance, for example a gas, a plasma, a fluid, a powder and/or a solid. To conduct a medium, the adapter may have one or more structural elements, for example conduits, line terminators, openings, conveyor screws, pumps and/or the like. The structural elements for media transmission may be part of the adapter, or may be connected with this so as to be releasable and relockable.

In one embodiment, the adapter may have a media storage unit that may be connected with structural elements to conduct the media. For example, such containers for storing the media may be designed as pressure containers for gases or storage containers for fluids or powders. The media storage units may be part of the adapter or be connected with said adapter so as to be releasable and relockable.

In one possible embodiment of the adapter, the adapter has a power source to operate camera electronics, signal transmission, motors, sensors, cooling, illumination or the like, which power source is designed to provide power via energy conversion. In particular, such power sources may have photovoltaic elements, induction coils, batteries, storage batteries, turbines, generators, thermoelectric elements, pressurized containers or the like. The structural elements of the power source may be part of the adapter, or may be connected with this so as to be releasable and relockable. In one embodiment, the adapter may be designed to transmit or generate its movements. To that end, the adapter may have movement transmission elements, for example couplings, shafts, connecting rods, Bowden cables, gears, pneumatic or hydraulic conduits and/or the like that, for example, connect the distal side of the adapter with the proximal side of the adapter, for example via openings in the adapter or the like. To generate movements, the adapter may have actuators—for example motors, electric motors or compressed air actuators. The elements for transmission and generation of movements may be part of the adapter, or may be connected with this so as to be releasable and relockable.

In one possible embodiment, the adapter is designed for the guidance and/or attachment of instruments through the adapter. To that end, the adapter may have openings, guide rollers, guide tubes, bearings, guidances, attachment elements and/or additional components suitable for the guidance and/or attachment of instruments through the adapter.

The adapter may be designed so that exchangeable optical windows that are transparent to electromagnetic radiation; power storage; power sources; power sinks; conductors; motors; media storage units; data storage units; sensors and/or transmission elements are exchangeable during operation of the adapter.

In one embodiment, one or more optical windows may be designed for exchange or for exchange during operation of the adapter, in order to simplify cleaning, sterilization, repair or servicing.

In one embodiment of the adapter, the clearance formed for the coupling with at least one part of a distal camera head end may have at least one coupling face that is designed to couple with at least one coupling face of the distal camera head end. Furthermore, the clearance formed for coupling with at least one part of a proximal endoscope end may have at least one coupling face that is designed to couple with at least one coupling face of the proximal endoscope end. In one possible embodiment, the inner wall has coupling faces both on its inside and on its outside, which coupling faces are designed to couple the endoscope and camera head. The coupling faces may be cylindrical, for example.

In one possible embodiment of the adapter, at least one of the coupling faces is of cylindrical design. Here, "cylindrical" is to be understood in the broadest sense, meaning as the derived cylindrical shell face of a cylinder that is defined by two parallel, flat, congruent surfaces and a shell surface or, respectively, cylinder surface. In particular, the term "cylindrical" thus also encompasses prismatic but also circularly cylindrical surfaces. In one adapter system, the endoscope, camera head and adapter preferably have respective coupling faces that are preferably matched to one another, such that a coupling between the coupling faces increases a coupling strength between the adapter and endoscope or, respectively, the camera head. A stronger coupling between endoscope, adapter and camera head may hereby be established that enables a more stable system overall.

In one possible embodiment of the adapter, at least one of the coupling faces is executed so as to couple at at least two points, meaning that the coupling face has two coupling sub-faces that are arranged at an axial distance from one another. In one alternative embodiment, two or more coupling sub-faces may also adjoin one another or have an axial and/or radial separation from one another. The coupling sub-faces may be cylindrical coupling sub-faces. The coupling sub-faces may also be of conical design. Multiple adjoining coupling sub-faces may also have an angle relative to one another so that a cross section tapering or cross section widening along the axial direction results, for example for the clearance enclosed by said coupling sub-faces. The coupling sub-faces may also have freeform faces. The coupling sub-faces may be designed such that they generate a cross section of a clearance varying in the axial direction, whereby an introduction of an endoscope or camera head that is to be coupled into the clearance may be simplified. In this case, undercuts are to be avoided.

In one embodiment of the adapter, at least one of the coupling faces or their coupling sub-faces may be designed such that a cross section varying along the axial direction results in at least one of the clearances.

In one possible embodiment of the adapter, at least one of the coupling faces is of conical design. In a further embodiment, at least one coupling sub-face of a coupling face is of conical design.

In one embodiment, the coupling faces may be cylindrical surfaces with varying diameters, which surfaces are connected with one another via conical transition surfaces. Upon coupling the adapter, greater mechanical play hereby exists at the start, which reduces later upon further coupling if all cylindrical coupling faces engage. This arrangement can close with very low force and is secure against twisting and seizing.

In one possible embodiment, the adapter has at least one rotation safeguard that is designed to prevent a rotation of an endoscope and/or camera head coupled with the adapter. For example, the rotation safeguard may be a hole, a bore or the like connected to a bolt, pin or the like adapted to this.

In one embodiment of the adapter, a rotation safeguard may be activatable and deactivatable. For example, a switching between an activated and non-activated state may be realized in that the rotation safeguard has movable structural elements that may be moved out of the engagement region of the rotation safeguard given a closed coupling. In one embodiment, the moving structural element may be designed so that the rotation safeguard forms a detent.

In one possible embodiment of the adapter system, endoscopes that are executed to be secured against rotation may be connected to the adapter so as to be secured against rotation, and endoscopes that are executed to not be secured against rotation may be connected to the adapter so as to not be secured against rotation. For example, such a different embodiment may take place in that rotation-secured endoscopes have a rotation-securing element such as a clearance hole or a radial groove that engages with a pin, bolt or the like at the adapter, and instead of the rotation-securing element an endoscope that is not rotation-secured has a clearance that enables a mutual rotation of the adapter and endoscope.

In one embodiment of the adapter system, camera heads executed so as to be rotation-secured may be connected to the adapter so as to be rotationally secure, and camera heads executed so as to not be rotation-secured may be connected to the adapter so as to not be rotationally secure.

In one possible embodiment of the adapter, the adapter has coupling faces with coupling sub-faces that are not rotation surfaces (meaning geometric faces) that may not be generated via rotation around an axis of a curve lying in a plane, which axis is arranged orthogonal to the plane. Given this design, securing—in terms of rotation—the adapter to an endoscope to be coupled and/or to a camera head to be coupled may be achieved via the broken rotational symmetry. The rotation safeguard for an adapter system made up of the adapter and endoscope or camera head may thus also result from the shape of the clearance and the shape of the endoscope or camera head in that these have a shape that forms no rotation surface; i.e., in that a rotation is prevented in an inserted state of the endoscope or camera head in one of the clearances of the adapter due to the shapes matched to one another.

In one embodiment of the adapter, the adapter may have at least one locking device that is designed to lock the endoscope and/or the camera head to the adapter so that it is releasable and relockable.

In one possible embodiment, the adapter has a sterile covering to cover the camera head. The covering is designed to surround the camera head so as to be sterile. The covering may be attached to the adapter, for example to the outer wall. Alternatively, the outer wall may also have an attachment device to which a covering may be attached.

In one embodiment, the adapter may have at least one optical conductor to transmit exposure light between the proximal end of the adapter and distal end of the adapter. In the adapter system—which preferably has the endoscope, the adapter and the camera head—the exposure light may be transmitted through the adapter to the distal end of the endoscope and be radiated there to an object to be illuminated, which object reflects light that is directed through the endoscope and the adapter to the camera head.

In one possible embodiment, the adapter has at least one electrical conductor to transmit electrical signals or electrical power, for example between the proximal end of the adapter and distal end of the adapter. For example, the energy may be used for measurement, for operation of light sources or for electrical stimulation.

The adapter may also have one or more optical and electrical conductors.

The adapter system may be designed to transmit and/or generate electromagnetic radiation. The adapter, the endoscope or the camera head may have a radiation source to generate electromagnetic radiation. The radiation source may have light-emitting diodes, laser diodes, lasers, infrared radiators, radio transmitters or the like. The adapter may have openings, windows, optical conductors, waveguides, antennas or the like to transmit electromagnetic radiation. The elements for generation and transmission of electromagnetic radiation may be connected with the adapter, the endoscope or the camera head permanently, or so as to be releasable and relockable. For example, the electromagnetic radiation may serve for diagnostic or therapeutic exposure or illumination; for image generation; and for measurements such as distance measurements, size measurement, topography measurements, radar measurements and/or radar mapping.

In one possible embodiment, the adapter system is designed for measurement of at least one physical variable. For this, the adapter, the endoscope or the camera head may have a sensor. For example, such measured physical variables may be temperature; pressure; time; separations;

lengths; movements; position; orientation; horizontal position; moisture; exposure strength; or sound pressure. Suitable sensors may be, for example, Hall sensors, thermal sensors, microphones, GPS receivers, photometers, or triangulation sensors. The sensor may be connected with the adapter, the endoscope or camera head permanently or so as to be releasable and relockable. For example, the measurement may serve for the detection of usage durations, sterilization data or wear data that may be automatically or manually evaluable.

In one embodiment, the adapter system may have a data storage unit to store measurement data, usage data, wear data, treatment data, image information, executable programs or the like. The data storage may be connected with the adapter, the endoscope or camera head permanently or so as to be releasable and relockable.

The data stored in a data storage may be generated, read out, processed further, transferred, overwritten, deleted or executed as a program by suitable structural elements. Cited structural elements may form a component of the adapter, endoscope or camera head, or may not form a component of the adapter system.

For example, programs stored in the data storage unit may serve to program a processing unit via the components of the adapter system that comprise the data storage unit. A processing unit for the most varied system configurations and/or operating states of the adapter system may thereby be suitably programmed. A cited processing unit may form a component of the adapter, endoscope or camera head, or may not form a component of the adapter system.

In one possible embodiment, the adapter system has a processing unit that is designed to execute programs. For example, such executable programs may serve for signal transmission, signal processing, control of storage processes, image processing, image recognition, telecommunications, movement control, control, measurement or data acquisition for diagnostic or therapeutic applications. For example, the processing unit may have microprocessors, digital signal processors (DSPs), FPGAs or ASICs. The processing unit may be connected with the adapter, the endoscope or camera head permanently or so as to be releasable and relockable.

In one embodiment, the adapter system may have at least one element to detect its position via a navigation system. Such elements to detect its position may be magnets, gyrosensors, transponders, reflectors, markings or optically visible shape elements. Elements to detect the position may be connected with the adapter, the endoscope or camera head permanently or so as to be releasable and relockable.

In one possible embodiment, the adapter system has a control element to control and/or activate camera functions or endoscope functions. For example, control elements may be designed to set a focus, select functions in a menu structure; and to take a still image or capture video and reproduce it; or to conduct a balance. Control elements may be connected with the adapter, the endoscope or camera head permanently or so as to be releasable and relockable.

In one embodiment, the adapter system may be designed for use with a manipulator or robot system. For this, the adapter system may have mounts and interfaces for signal transmission, controls, media transfer, force transfer, position detection, operating state detection and the like. Mounts and interfaces may be connected with the adapter, the endoscope or camera head permanently or so as to be releasable and relockable.

Furthermore, the invention also concerns the use of an adapter to couple an endoscope or stereo endoscope with a camera head. The stereo endoscope and the camera head are to be aligned with one another based on the double optical conductor. For this, the embodiment with the rotation safeguard is preferably used. The rotation safeguard may be part of the adapter or part of an adapter system made up of endoscope, adapter and camera head, wherein parts of the rotation safeguard are aligned to the endoscope, adapter and camera head.

The invention also relates to an adapter system made up of endoscope, adapter and camera head. The proximal end of the endoscope, the adapter and the distal end of the camera head are matched to one another so that the adapter may couple with at least one part of the proximal end of the endoscope and with a part of the distal end of the camera head. The beam path through the adapter system is hereby only slightly extended, since only a relatively thin optical window extends the beam path, and otherwise the endoscope and the camera head are coupled with the adapter so that said adapter separates the endoscope and the camera head. The separation may be germ-proof and comprise a covering for the camera head and components connected with this in order to separate the proximal side and the distal side from one another so as to maintain sterility, and thus to achieve an externally sterile adapter system.

In one possible embodiment of the adapter system, the camera head, the adapter and/or the endoscope has a power sink for heat dissipation. In particular, such power sinks may have cooling bodies, evaporators, radiators, thermoelectric elements or heat transmitters. The structural elements of the power sink may be part of an adapter, of the endoscope and/or of the camera head, or may be connected with one or more of these so as to be releasable and relockable.

In one embodiment, the adapter system may have an element for heating. For example, an element for heating may prevent a fogging of optical components. An element for heating may be a component of the endoscope, adapter or camera head, or be connected with the endoscope, adapter or camera head so as to be releasable and relockable.

In one possible embodiment of the adapter system, the camera head, the adapter and/or the endoscope has an energy storage unit. In particular, such energy storage units may have fuel cells, rechargeable batteries, heat storage, springs or flywheels. The structural elements of the energy storage may be part of the adapter, of the endoscope and/or of the camera head, or may be connected with one or more of these so as to be releasable and relockable.

In one embodiment of the adapter system, the adapter, the endoscope and/or the camera head may have a light source. The light source may be part of the adapter, of the endoscope and/or of the camera head, or may be connected with one or more of these so as to be releasable and relockable.

In one possible embodiment of the adapter system, the camera head, the adapter and/or the endoscope has a power source to operate camera electronics, signal transmission, motors, sensors, cooling, illumination or the like, which power source is designed to provide power via energy conversion. In particular, such power sources may have photovoltaic elements, induction coils, batteries, storage batteries, turbines, generators, thermoelectric elements or the like. The structural elements of the power source may be part of the adapter, of the endoscope and/or of the camera head, or may be connected with one or more of these so as to be releasable and relockable.

The use of an adapter for coupling a stereo endoscope with a camera head is particularly advantageous since, in the case of stereo endoscopes, an extension of the adapter system length is associated with high technical cost and a marked degradation of the image quality. Therefore, in the case of known stereo endoscopes according to the prior art, either work must be conducted without a sterile adapter, or—for space reasons—a control ring for focusing cannot be mounted at the typical and most advantageous position, near the distal end of the camera head. In other words, the proven and widespread basic design of a two-dimensional (2D) endoscopy system with a manual focus near the distal end could previously only be used for stereoendoscopy if a sterile intermediate adapter was omitted. In contrast to this, the invention enables the design of such a sterile stereoendoscopic system. Significantly greater operating comfort may thereby be achieved than was previously typical with sterile stereoscopic tasks.

In the case of two-channel stereo endoscopes, in addition to the axial alignment, a horizontal alignment of camera head and stereo endoscope is also required. For this, in one possible embodiment the adapter has a rotation safeguard that prevents a mutual rotation of the endoscope, adapter and camera head. Examples of a rotation safeguard include pins that are positioned in holes, oblong holes or grooves given a coupled adapter. The rotation safeguard may also have projections that engage in depressions. Furthermore, screws, spring clamps, clamps, latching connections, magnet connections and the like may be executed so that they form a rotation safeguard. The rotation safeguard may also be generated by a bayonet joint. Furthermore, a rotation safeguard may be achieved if coupling faces or coupling subfaces are designed as non-rotation surfaces.

In addition to the coupling faces, the invention has a locking device with locking elements for releasable and relockable locking of the endoscope to the adapter, and additionally for releasable and relockable locking of the camera head to the adapter. For this, all known locking elements may be used, such as screws, spring clips, clips, bayonet joints, latching connections, magnet connections and the like. In one embodiment of the adapter system made up of the endoscope, adapter and camera head, the endoscope has a screw with a fixing nut near its proximal end for locking to the adapter, while the camera head has near its distal end a sprung bayonet joint for locking the camera head to the adapter. Control elements for locking the endoscope may alternatively be attached to the adapter. Moreover, control elements for locking the camera head may alternatively be attached to the adapter or camera head.

The adapter is preferably designed so that—upon coupling the adapter with the endoscope or the camera head—the coupling faces first engage insofar as that both components to be coupled are aligned axially and radial displacements are prevented, while axial displacement and rotation are still possible. Insofar as they are present, the rotation safeguard or rotation safeguards preferably only engage afterward, and the coupling process is terminated by activating the locking device or devices to lock the adapter to the endoscope or to the camera head. The adapter enables large guide lengths on the coupling faces, and the modules to be coupled may already be guided well at the beginning of the coupling of the adapter. Even if the endoscope or the camera head are connected with the adapter, rotated at a random rotation angle, after partial coupling of the adapter the correct orientation may be established easily via mutual rotation, and without significant concentration by the operator. The rotation safeguard may be designed such that, given a random rotation of the modules to be coupled that are brought together with slight pressure, the adapter blocks or catches in the correct rotation position. In particular in the case of stereo endoscopes, the handling of the adapter may take place significantly more easily and intuitively, and the risk of operating errors may be markedly reduced.

Furthermore, the radial structural size may also be reduced via use of the adapter in an adapter system made up of an endoscope, adapter and camera head. Since, if suitably executed, the coupling faces at the endoscope, camera head and adapter mutually support one another mechanically, low material thicknesses may be used in the region of the coupling faces, and in spite of this a high strength and rigidity of the adapter may be achieved. The adapter may be designed for a single use, for example be made of plastic. In this case, the strength gain is particularly advantageous. The increase of the rigidity may simultaneously improve the image quality as a result of more precise coupling.

Furthermore, via the small structural size of the adapter system made up of endoscope, adapter and camera head, which small structural size is achieved by means of the adapter, a very advantageous ratio of the lever lengths of the adapter to those of the adapter system may be achieved. An additional gain in strength and rigidity may thereby be provided.

Furthermore, the adapter enables a very simple mechanical structure having a small number of moving modules, whereby hygienic requirements such as sterility and cleanliness may be better satisfied. Moreover, product reliability is thereby increased, and production costs are reduced.

The adapter may be executed to be sterile for a one-time use, or sterilizable for repeated use. The adapter may be releasable or permanently connected with a sterile covering for the camera head and cable. Such a releasable and relockable connection may be realized via an elastic ring or adhesive band on the covering. Furthermore, such a releasable connection may be executed as a locking connection, bayonet joint, screw joint or magnetic attachment. Such sterile coverings may be designed for one-time or multiple use.

Feed-throughs for light-conducting fibers and electrical contacts may also be integrated in the adapter in order to transfer exposure light and electrical signals via the adapter.

The adapter may have sensors for identification of connected endoscopes or the adapter or, respectively, the combination of both via the camera head. The adapter may also have conductors to conduct signals for such identifications. For example, windows to let through electromagnetic signals may be arranged on or in the adapter. The adapter may also have transponders to transmit and/or receive electromagnetic signals. The adapter may also have electronic circuits. The adapter may be designed to identify a coupled endoscope and/or coupled camera heads. The adapter may be designed to evaluate, to process, to convert and/or to relay such identifications. The adapter may be designed to send its own identification to the coupled endoscope and/or the coupled camera head. The identification of the adapter can be used by the endoscope and/or camera head for the adaptation of parameters specific to an adapter system.

In addition to its use as a sterile or sterilizable adapter, the adapter can also be used for non-sterile applications. Such a non-sterile use is, for example, the use for adaptation of different adapter systems, or to achieve better servicing possibilities as a result of the ability to exchange components.

The invention is explained in detail using exemplary embodiments schematically depicted in the figures.

DETAILED DESCRIPTION

Figure 1:
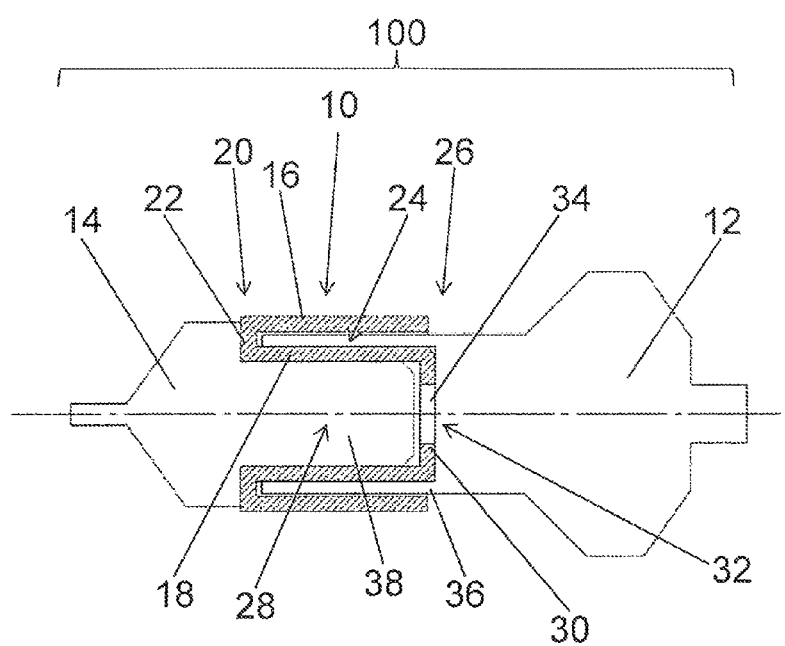
FIG. 1 shows a schematic section depiction of a first exemplary embodiment of an adapter with a coupled camera head and endoscope.

FIG. 1 shows a schematic section depiction of a first exemplary embodiment of an adapter 10 with a coupled camera head 12 and endoscope 14, i.e. of an adapter system 100. The camera head 12 is mechanically and optically connected with the endoscope 14 via the adapter 10 so as to be releasable and relockable.

The adapter 10 has an outer wall 16 and an inner wall 18 that, in a first exemplary embodiment of the adapter 10, are arranged concentrically with one another and are connected with one another via a connecting wall 22 at their distal end 20. In this exemplary embodiment, a clearance 24 in the shape of a hollow cylindrical shell, open at the proximal side of the adapter, is hereby created between outer wall 16 and inner wall 18. Alternatively, another shape of a clearance 24 may also be formed, for example with a varying cross section along the axial direction, such that different lateral separations between outer wall 16 and inner wall 18 arise along the axial direction. In the example shown, the distal end 20 of the outer wall 16 and inner wall 18 is also the distal end of the adapter 10. Alternatively, for example, one of the walls 16 or 18 may also be longer on the distal side, such that the walls 16 and 18 have no common distal end (not shown). For example, the connecting wall 22 may also be arranged not at the distal end 20, but rather in the immediate vicinity of the distal end 20, such that a smaller projection of one of the two walls 16 and 18 is formed.

The inner wall 18 extends between its distal end 20 and a proximal end 26, which in the example shown is the proximal end of the adapter 10. At the proximal end 26 of the inner wall 18, a clearance 28 enclosed by the inner wall 18 is sealed by a coupling wall 30, such that the clearance 28 enclosed by the inner wall 18 is open on the distal side of the adapter 10. In the example shown, the coupling wall 30 has an opening 32 in which an optical window 34 is arranged. The optical window 34 serves to transmit radiation in the visible wavelength range between the distal side and proximal side of the adapter 10.

In the example shown, the clearance 24 formed by outer wall 16 and inner wall 18 is formed such that a part of a distal camera head end 36 may protrude into it and be coupled, meaning that the clearance 24 is matched to the shape of a part of the distal camera head end 36. In this case, the clearance 28 formed by inner wall 18 is formed such that a part of a proximal endoscope end 38 may protrude into it and be coupled, meaning that the clearance 28 is matched to the shape of a part of the proximal endoscope end 38. Alternatively, clearance 24 may also be designed for the coupling of the proximal endoscope end 38, and for this may be open on the distal side of the adapter 10 (see FIG. 11), and clearance 28 may be designed to couple the distal endoscope end 36 and to that end may be open on the proximal side of the adapter 10 (see FIG. 11).

A hermetic—or at least germ-proof—separation between the proximal side and the distal side of the adapter 10 may be achieved with the design of the adapter 10 in FIG. 1, whereby it is possible to keep a sterile side separate from a non-sterile side, and thus to keep the sterile side sterile.

Figure 2:
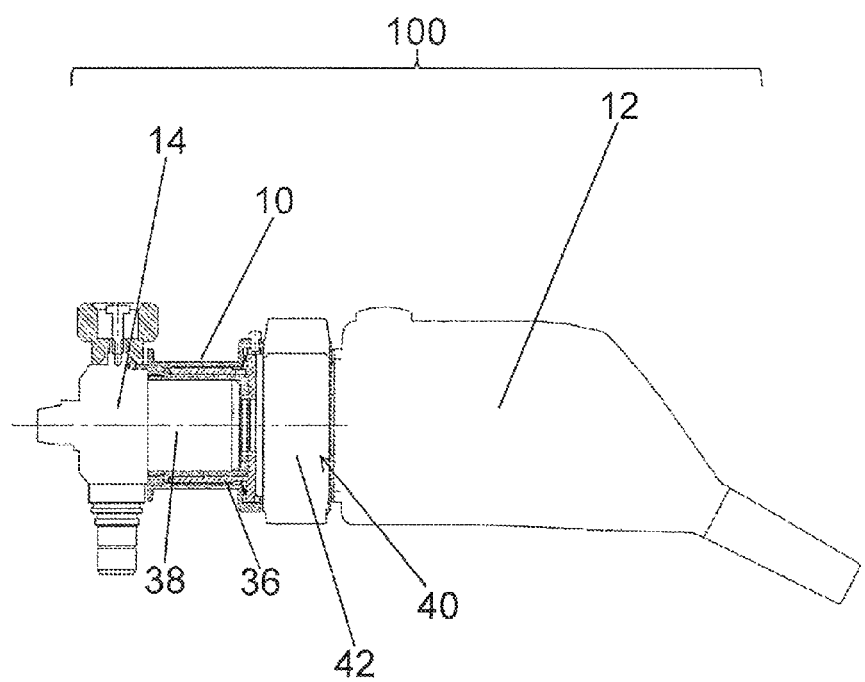
FIG. 2 shows a second exemplary embodiment of an adapter with a coupled camera head and endoscope.

FIG. 2 shows a second exemplary embodiment of an adapter system 100 with adapter 10 in a state coupled with camera head 12 and endoscope 14. The adapter system 100 comprises a focusing device 40 that—via a focus control ring 42 operable by a user—enables a beam path within the adapter 10 to be focused on an image-taking device (not shown) contained in the camera head 12. Because of the compact design of the adapter system 100, the focus control ring 42 of the focusing device 40 may be mounted at an ergonomic and technically advantageous point near the distal camera head end 36.

Figure 3:
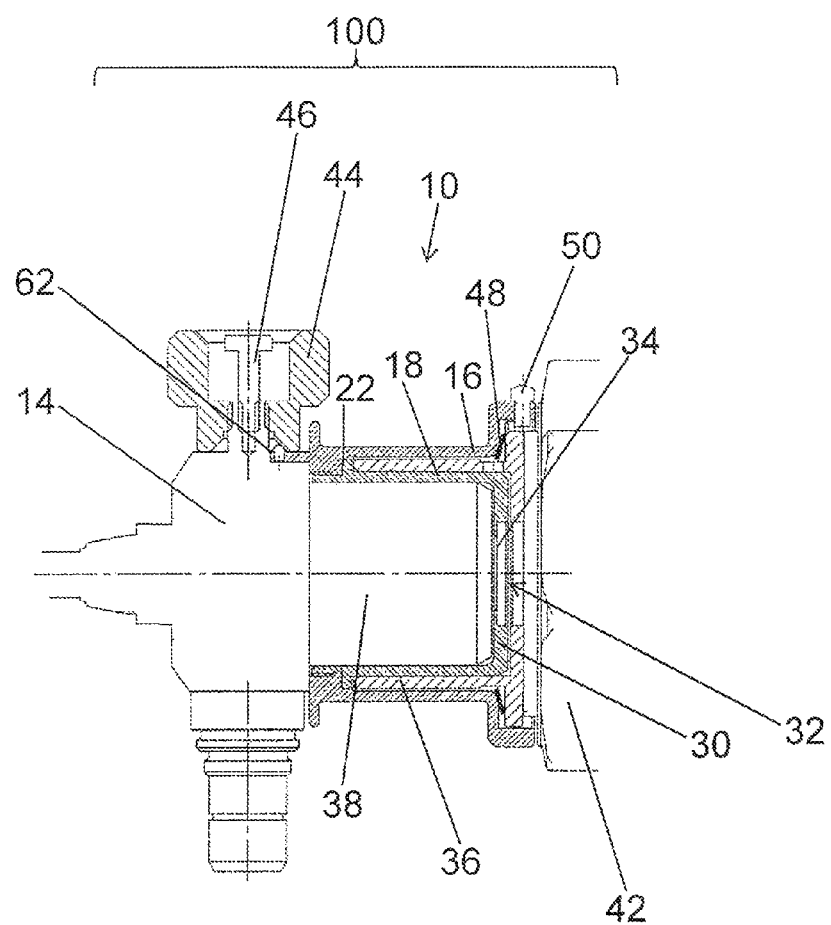
FIG. 3 shows an enlarged section from FIG. 2.

FIG. 3 shows an enlarged section from FIG. 2. The endoscope 14 has a fixing nut 44 to lock the adapter 10 to the endoscope 14. In order to achieve a good bathing during sterilization, the fixing nut 44 may be loosened before sterilization. A loss protection device 46 against losing the fixing nut 44 holds the fixing nut 44 in the loosened state together with the endoscope 14. A disk spring 48 attached to the camera head 12 generates a mechanical compression force between adapter 10 and the camera head 12. The proximal bolt 50 to fix the camera head 12 thereby engages with the force of the disk spring 48 in the receiving face 52 of the bayonet joint 54 shown in FIG. 9.

Figure 4:
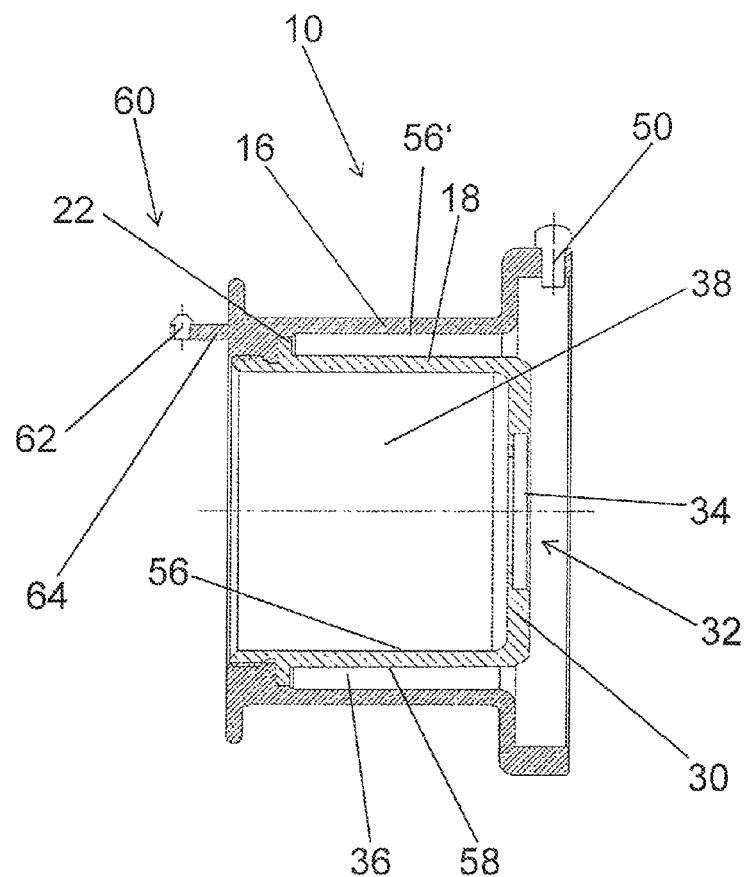
FIG. 4 shows a section depiction of the second exemplary embodiment of an adapter.
Figure 5:
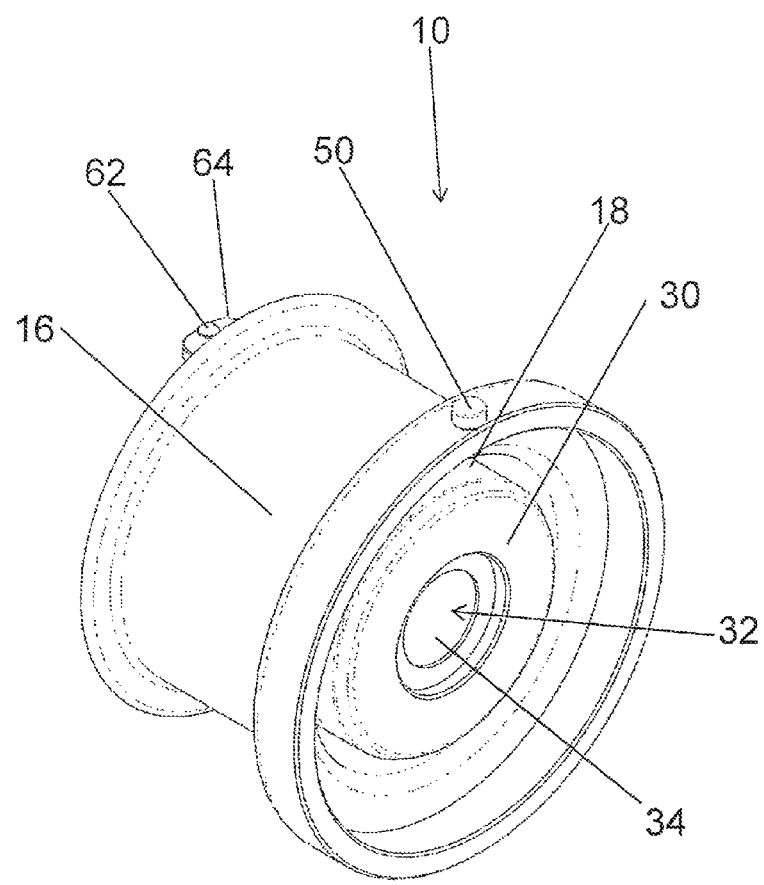
FIG. 5 shows a perspective depiction with a viewing direction towards the proximal end of the second exemplary embodiment of the adapter.
Figure 6:
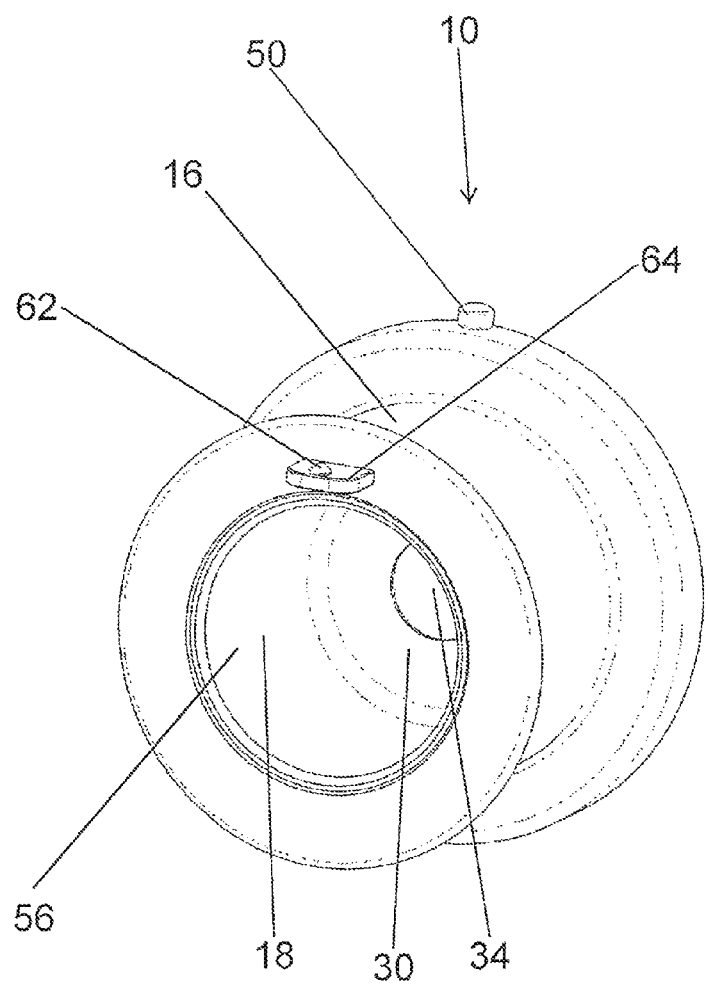
FIG. 6 shows a perspective depiction with a viewing direction towards the distal end of the second exemplary embodiment of the adapter.

FIG. 4 shows a section depiction of the second exemplary embodiment of an adapter 10. Perspective depictions of this second exemplary embodiment are shown in FIG. 5 and FIG. 6. The outer wall 16 in the example shown is connected with the inner wall 18 by the connecting wall 22, so as to be releasable. Near the proximal end of the adapter 10, the clearance 38 enclosed by the inner wall 18 is sealed by the coupling wall 30. The optical window 34 is arranged in the opening 32 for light transmission. In the example shown, the inner wall 18 has an inner coupling face 56 and an outer coupling face 58. The inner coupling face 56 is designed to couple with a part of the proximal endoscope end 38, and the outer coupling face 58 is designed to couple with a part of the distal camera head end 36. The outer wall 16 also has on its inside an inner coupling face 56' that is designed to be coupled with a part of the distal camera head end 36. Alternatively, the inside of the outer wall 16 may also be executed without a coupling face. Multiple coupling sub-faces may also be arranged on the insides of the inner wall 18 and outer wall 16 and on the outside of the inner wall 18. The coupling sub-faces may be arranged separated axially and/or radially or possibly laterally, such that a coupling between endoscope 14 and adapter 10 and camera head 12 and adapter 10 is created only at specific faces or points. A lateral separation of the coupling sub-faces may occur when a shape deviates from a circular cylindrical shape, for example a prismatic shape.

Near the distal end 60 of the adapter 10, the adapter 10 has a distal bolt 62 to fix the endoscope 14 to the adapter 10. In the example shown, the distal bolt 62 is attached to a rotation safeguard clip 64, which prevents a rotation of the endoscope 14 connected to the adapter 10. Located near the proximal end of the adapter 10 is the proximal bolt 50 for locking the camera head 12 to the adapter 10. As shown, the adapter 10 may be produced from two rotating parts and may thereby be separable. However, a production from only one part or more than two parts is also possible. The multiple parts may also be rotating parts.

Figure 7:
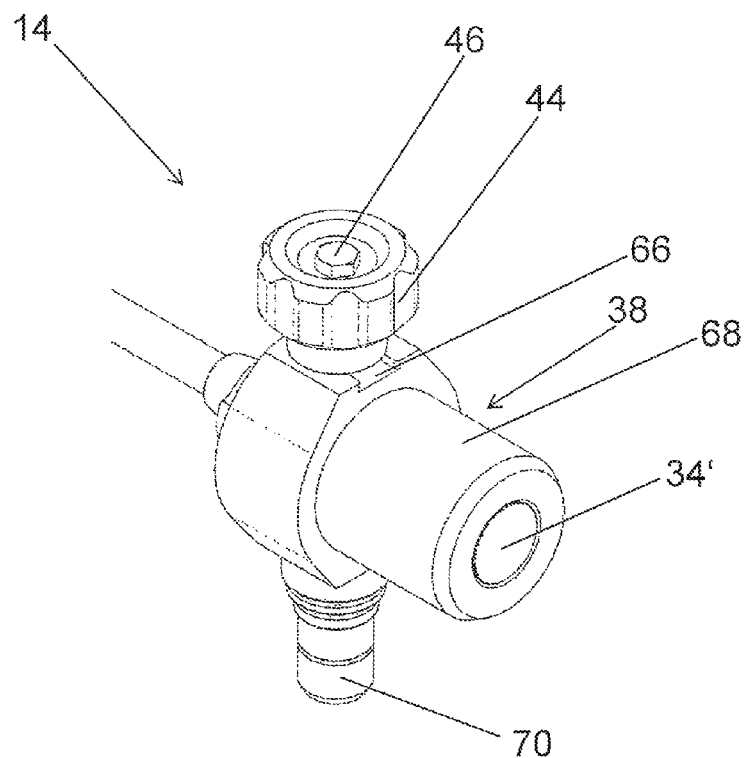
FIG. 7 shows a perspective depiction with a viewing direction towards the proximal end of an endoscope.

FIG. 7 shows a perspective depiction with a viewing direction towards the proximal end of an endoscope 14. The endoscope 14 has the fixing nut 44 to lock the endoscope 14 to the adapter 10. The loss prevention 46 prevents the fixing nut 44 from separating from the endoscope 14 in a loosened state and being lost. In the loosened state, the screw thread flanks of the fixing nut 44 are accessible to a sterilizing agent, for example a disinfecting agent or another disinfecting medium. The shape of a groove 66 is matched to the rotation safeguard clip 60 (see FIG. 6), whereby a coupled adapter 10 prevents a mutual rotation of endoscope 14 and adapter 10. In this exemplary embodiment, the coupling face 68 of the endoscope 14 is designed in the shape of a circular cylinder, but may also have other shapes, for example a cylindrical shape, a conical shape or other shapes. Here, "cylindrical" is to be understood in the broadest sense and, for example, also encompasses prismatic shapes. The shape may also have cross section changes in the axial direction, wherein the shape of the proximal endoscope end 38 is matched to the shape of the clearance 28 of the first exemplary embodiment of the adapter 10 (see FIG. 1) in order to enable a coupling. The shape of the proximal endoscope end 38 may also be of different design in order to match an alternative exemplary embodiment of the adapter 10 (see FIG. 11).

In the state in which it is coupled with the adapter 10, an optical window 34' of the endoscope 14 adjoins the optical window 34 of the adapter 10. The beam path is hereby extended through the adapter 10 only by the thickness of the optical window 34 of the adapter 10. It is also possible to execute an adapter 10 without optical window 34 so that, in this case, the optical window 34' of the endoscope 14 may immediately adjoin—through the opening 32 of the adapter 10—an optical window 34" of the camera head 12 (see FIG. 8), such that the adapter 10 does not affect the length of the beam path.

The endoscope 14 shown has a connection 70 for an optical conductor cable in order to supply exposure light to the endoscope 14 and thus—in the coupled state of the endoscope 14 with the adapter 10—to the adapter system 100.

Figure 8:
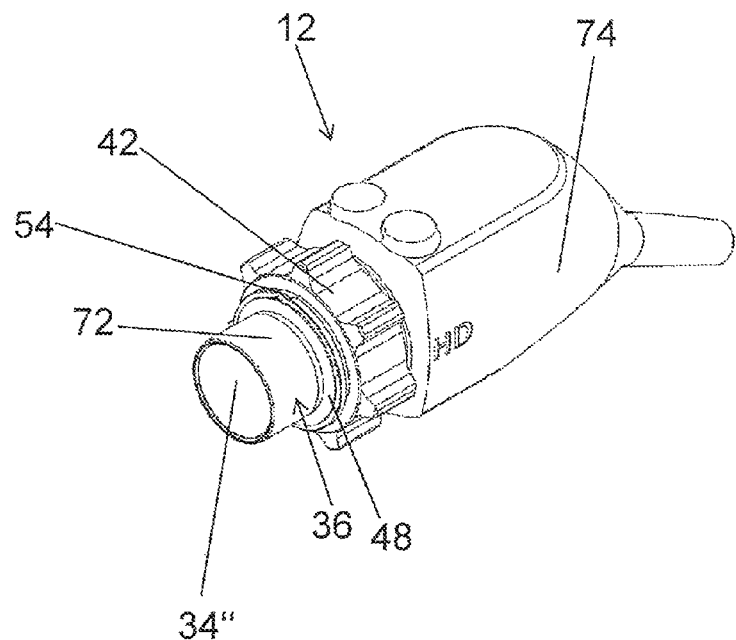
FIG. 8 shows a perspective depiction of a camera head.

FIG. 8 shows a perspective depiction of a camera head 12. The coupling face 72 of the proximal camera head end 36 is matched to the clearance 24 of the first exemplary embodiment of the adapter 10 (see FIG. 1)—which clearance 24 is designed for coupling of the proximal camera head end 36—and thus may be coupled with the adapter 10. The adapter 10 may be locked in the bayonet joint 54 by means of the proximal bolt 50 (see FIG. 6). A force for a defined engagement of the proximal bolt 50 (see FIG. 6) in the bayonet joint 54 is generated by disk spring 48. Due to its rotationally secured design, the camera head 12 is suitable for use with stereo endoscopes (not shown). Near the distal end of the camera housing 74, the camera head 12 has a focus control ring 42 that serves to focus a beam path onto an image acquisition device (not shown) comprised in the camera head 12.

Figure 9:
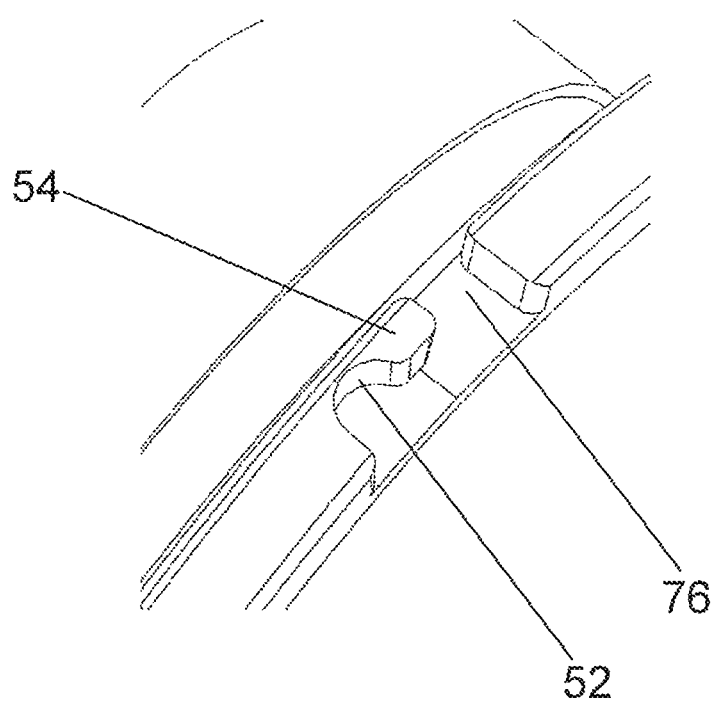
FIG. 9 shows a schematic depiction of an exemplary embodiment of a bayonet joint at the camera head.

FIG. 9 shows a schematic depiction of an exemplary embodiment of a bayonet joint 54 at the camera head 12. Via an insertion groove 76, an attachment element (for example a bolt, a pin or the like) located at the adapter 10 may be introduced into the bayonet joint 54. After mutual rotation of camera head 12 and adapter 10, this attachment element engages in the receiving face 52. The catch force may be generated via a suitable elastic element.

Figure 10:
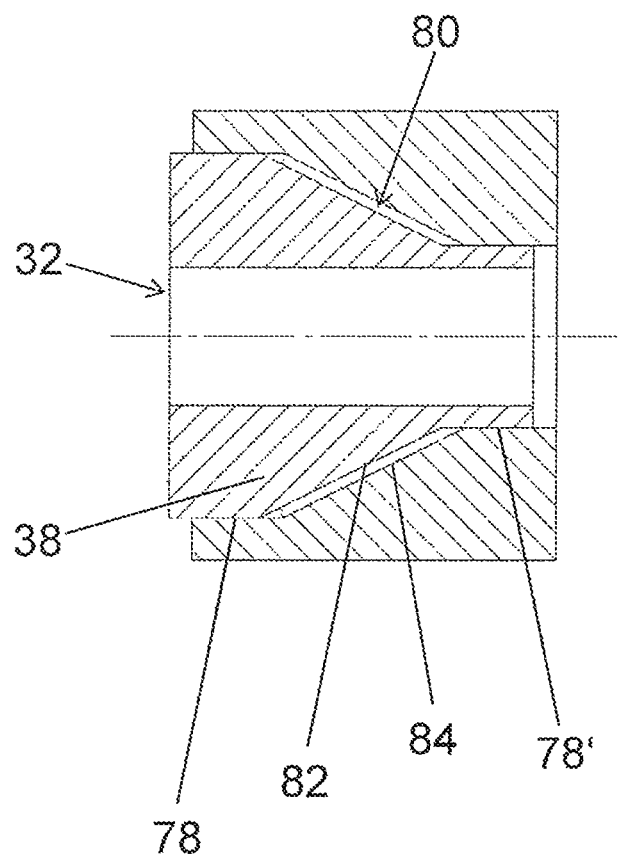
FIG. 10 shows a schematic section depiction through a coupling face coupling at two points.

FIG. 10 shows a schematic section depiction of a partial section of an adapter 10 through a coupling face 78, 78' coupling at two points. In an alternative exemplary embodiment—not shown—the coupling face may also be executed to couple at three or more points. In the example shown, a proximal endoscope end 38 is inserted partially into a clearance of the adapter 10 that is open at the distal side. Instead of the proximal endoscope end 38, a distal camera head end 36 may also alternatively be inserted into a clearance of the adapter 10 (not shown) that is open at the proximal side. The endoscope has an opening 32 through which a beam path (not shown) may be directed.

Figure 12:
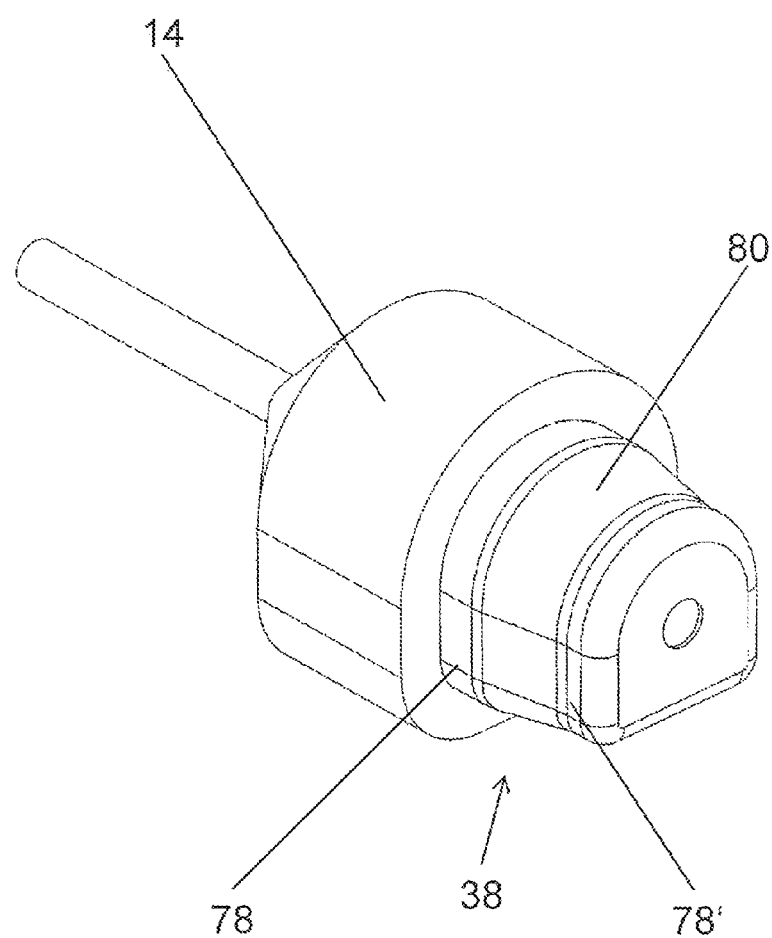
FIG. 12 shows a perspective depiction with a viewing direction towards the proximal end of an endoscope with a coupling face generating a rotation safeguard.

Two cylindrical coupling sub-faces 78 and 78' of a proximal endoscope end 38 are connected with one another by a conical transition 80 (see FIG. 12). In the example shown, the sub-face 82 of the endoscope 14 and the sub-face 84 of the adapter 10 are executed so as to not couple at the conical transition 80, so that a non-coupling axial segment results between the two coupling coupling sub-faces 78 and 78'.

It is particularly advantageous to design the coupling faces of adapter 10, endoscope 12 and camera head 14 to couple at two points in the manner shown in FIG. 10. An easy operation with little mechanical play is thereby enabled.

For example, the coupling faces may be magnetic and couple via a magnetic attraction of opposite coupling faces. Alternatively, coupling faces may also mechanically couple, for example due to the surface contour and friction forces occurring between the coupling faces. It is also possible to mix different coupling face types, i.e. mechanically and magnetically coupling coupling faces; for example, a coupling face at one point that couples mechanically and a coupling face at another point that couples magnetically may be used.

Figure 11:
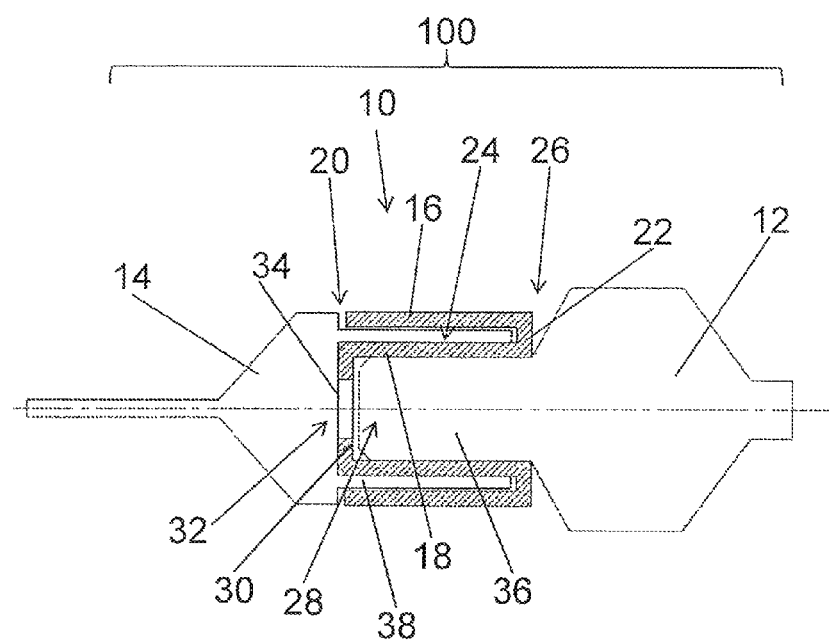
FIG. 11 shows a schematic section depiction of a third exemplary embodiment of an adapter with coupled camera head and endoscope.

FIG. 11 shows a third exemplary embodiment of an adapter 10. In contrast to the first exemplary embodiment of the adapter 10 from FIG. 1, in the third exemplary embodiment of the adapter 10, the clearance 24—which has the shape of a hollow cylindrical shell and is enclosed by outer wall 16 and inner wall 18—is open at the distal side, and the clearance 28 enclosed by the inner wall is open at the proximal side. This made possible in that the adapter 10 is turned over and the shapes of the proximal endoscope end 38 and of the distal end 36, which shapes are matched to the clearances 24 and 28 of the adapter 10, are aligned to the rotated adapter 10.

A part of the proximal endoscope end 38 is introduced into the clearance 24 open on the distal side. A part of the distal camera head end 36 is introduced into the clearance 28 open on the proximal side. The connecting wall 22, the coupling wall 30 and the optical window 34 produce a sterile separation between the distal side and proximal side of the adapter 10. In this case, the adapter 10 is germ-proof; no germs can arrive from the distal side of the adapter to the proximal side or vice versa. The third exemplary embodiment of the adapter 10 is in particular provided to produce a stable connection with camera heads with electro-motorized focusing.

FIG. 12 shows a perspective depiction with a viewing direction towards the proximal end of an endoscope 14, in which the coupling face 78, 78' of the endoscope is executed with cylindrical coupling sub-faces 78, 78' coupling at two points, which coupling sub-faces 78, 78' are connected with one another via a non-coupling conical transition 80. The shape of the coupling face 78, 78' enables a rotationally secured and easily pluggable coupling of the endoscope 14 to an adapter 10 shaped to match (see FIG. 10).

REFERENCE LIST

10 adapter
12 camera head
14 endoscope
16 outer wall
18 inner wall
20 distal end of the outer wall and inner wall
22 connecting wall
24 clearance situated between inner wall and outer wall
26 proximal end of the inner wall
28 clearance enclosed by the inner wall
30 coupling wall
32 opening
34, 34', 34" optical window
36 distal camera head end
38 proximal endoscope end
40 focusing device
42 focus control ring
44 fixing nut
46 loss prevention device
48 disk spring
50 proximal bolt
52 receptacle face
54 bayonet joint
56, 56' inner coupling face
58 outer coupling face
60 distal end of the adapter
62 distal bolt
64 rotation safeguard clip
66 groove
68 coupling face of the endoscope
70 connection for an optical conductor cable
72 coupling face of the camera head
74 camera housing
76 insertion groove
78, 78' two-point coupling face of the endoscope
80 conical transition
82 sub-face of the endoscope at the conical transition
84 sub-face of the adapter at the conical transition
100 adapter system

What is claimed is:
1. An adapter for the releasable and relockable coupling of an endoscope with a camera head, comprising:
    an inner wall, an outer wall, a connecting wall, and a coupling wall,
    wherein the inner wall encloses a clearance,
    wherein the outer wall surrounds the inner wall with at least a lateral separation to the inner wall so that a second clearance results between the inner wall and the outer wall,
    wherein the outer wall is connected with the inner wall via the connecting wall extending between the inner wall and the outer wall at or in an area of their first axial ends,
    wherein the coupling wall confines the clearance enclosed by the inner wall at or near a second axial end of the inner wall,
    wherein the clearance that is enclosed by the inner wall is open at a first axial side that is situated opposite the second axial end of the inner wall and the second clearance is open on a second axial side that is situated opposite the first axial end,
    wherein one of the clearances is designed for releasable and relockable coupling with at least a portion of a distal camera head end, and
    wherein the other of the clearances is designed for releasable and relockable coupling with at least a portion of a proximal endoscope end.

2. The adapter according to claim 1 that is germ-proof between an endoscope that can be arranged on a distal side of the adapter and a camera head that can be arranged on a proximal side of the adapter, in order to thus separate a sterile side from a non-sterile side and to keep the sterile side sterile in this way.

3. The adapter according to claim 1, wherein at least one of the clearances has a cross section varying along the axial direction and/or along a polar angle.

4. The adapter according to claim 1, wherein the adapter is designed to ensure that, in a state in which the adapter is coupled with endoscope and camera head, the parts of the proximal endoscope end and the parts of the distal camera head end that protrude into one of the respective clearances overlap along the axial direction of the adapter by at least 50% of an axial length of at least one of the clearances.

5. The adapter according to claim 1, wherein the coupling wall has at least one opening and/or at least one optical window that is designed to transmit radiation in the optical wavelength range.

6. The adapter according to claim 1,
    wherein the clearance formed for the coupling with at least one part of a distal camera head end has at least one coupling face that is designed to couple with at least one coupling face of the distal camera head end, and
    wherein the clearance formed for the coupling with at least one part of a proximal endoscope end has at least one coupling face that is designed to couple with at least one coupling face of the proximal endoscope end.

7. The adapter according to claim 6, wherein at least one of the coupling faces is designed to be cylindrical or in the form of a hollow cylindrical shell.

8. The adapter according to claim 6, wherein at least one of the coupling faces is designed to couple at at least two points and has at least two coupling sub-faces.

9. The adapter according to claim 6, wherein at least one of the coupling faces or their coupling sub-faces can be designed so that a cross section varying along the axial direction results in at least one of the clearances.

10. The adapter according to claim 1 that has at least one rotation safeguard that is designed to prevent a rotation of an endoscope and/or camera head coupled with the adapter.

11. The adapter according to claim 1 that has at least one locking device that is designed to lock the endoscope and/or camera head to the adapter so that they are releasable and relockable.

12. The adapter according to claim 1 that has a sterile covering to cover the camera head, wherein the covering is designed to enclose the camera head in a sterile manner.

13. The adapter according to claim 1, wherein the inner wall has coupling faces both on its inside and on its outside, wherein the coupling faces are designed to couple the inner wall with the endoscope and the camera head.

14. The adapter according to claim 1 that has at least one optical conductor to transmit exposure light and/or for optical signal transmission and/or at least one electrical conductor to transmit electrical signals and/or electrical power between the proximal side of the adapter and the distal side of the adapter.

15. A use of an adapter according to claim 1 for the coupling of a stereo endoscope with a camera head.

* * * * *